United States Patent
Egami

(10) Patent No.: US 10,434,103 B2
(45) Date of Patent: Oct. 8, 2019

(54) CRYSTAL OF 3,5-DISUBSTITUTED BENZENE ALKYNYL COMPOUND

(71) Applicant: TAIHO PHARMACEUTICAL CO., LTD., Tokyo (JP)

(72) Inventor: Kosuke Egami, Tokyo (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 15/562,455

(22) PCT Filed: Mar. 31, 2016

(86) PCT No.: PCT/JP2016/060844
§ 371 (c)(1),
(2) Date: Sep. 28, 2017

(87) PCT Pub. No.: WO2016/159327
PCT Pub. Date: Oct. 6, 2016

(65) Prior Publication Data
US 2018/0110782 A1    Apr. 26, 2018

(30) Foreign Application Priority Data
Mar. 31, 2015  (JP) ................................. 2015-070927

(51) Int. Cl.
| | | |
|---|---|---|
| A61K 31/519 | (2006.01) | |
| C07D 487/04 | (2006.01) | |
| C30B 29/58 | (2006.01) | |
| A61P 35/00 | (2006.01) | |
| A61K 9/00 | (2006.01) | |

(52) U.S. Cl.
CPC .......... *A61K 31/519* (2013.01); *A61K 9/0053* (2013.01); *A61P 35/00* (2018.01); *C07D 487/04* (2013.01); *C30B 29/58* (2013.01)

(58) Field of Classification Search
CPC .. C07D 487/04; A61K 9/0053; A61K 31/519; A61P 35/00; C30B 29/58
USPC ...................................................... 514/262.1
See application file for complete search history.

(56) References Cited

U.S. PATENT DOCUMENTS

| | | |
|---|---|---|
| 8,772,283 B2 | 7/2014 | Nakamura et al. |
| 2012/0101064 A1 | 4/2012 | Howard et al. |
| 2013/0061403 A1 | 3/2013 | Bringewatt et al. |
| 2014/0005185 A1 | 1/2014 | Nakamura et al. |
| 2014/0343035 A1 | 11/2014 | Sagara et al. |
| 2015/0166544 A1 | 6/2015 | Zhang et al. |
| 2016/0136168 A1 | 5/2016 | Sootome |
| 2016/0193210 A1 | 7/2016 | Ochiiwa et al. |
| 2017/0035773 A1 | 2/2017 | Tomimatsu |
| 2017/0252317 A1 | 9/2017 | Lyssikatos et al. |

FOREIGN PATENT DOCUMENTS

| | | |
|---|---|---|
| EA | 201101566 A1 | 5/2012 |
| EP | 3279202 A1 | 7/2018 |
| JP | 2011-524888 A | 9/2011 |
| JP | 2016-104762 A | 9/2016 |
| RU | 20098127883 A | 7/2009 |
| RU | 2428421 C2 | 12/2009 |
| WO | 2007041712 A1 | 4/2007 |
| WO | 2007087395 A2 | 8/2007 |
| WO | 2008077557 A1 | 7/2008 |
| WO | 2008121742 A2 | 10/2008 |
| WO | 2009153592 A1 | 12/2009 |
| WO | 2010043865 A1 | 4/2010 |
| WO | 2011093672 A2 | 8/2011 |
| WO | 2011115937 A1 | 9/2011 |
| WO | 2011153514 A2 | 12/2011 |
| WO | 2012137870 A1 | 10/2012 |
| WO | 2013108809 A1 | 7/2013 |
| WO | 2014138364 A2 | 9/2014 |
| WO | 2014172644 A2 | 10/2014 |
| WO | 2015008839 A1 | 1/2015 |
| WO | 2015008844 A1 | 1/2015 |
| WO | 2016159327 A1 | 10/2016 |
| WO | 2017150725 A1 | 9/2017 |

OTHER PUBLICATIONS

Office Action dated Apr. 24, 2018 for the corresponding RU patent application No. 2017134584, 15 pages.
Lectures of Experimental Chemistry (continued) 2 Separation and purification, 1967, pp. 159-162, 184-193.
Handbook of Solvents, 1985, pp. 47-51.
Version 4 Lectures on experimental chemistry 1 Basic operation I, 1990, pp. 184-189.
Impurities: Guideline for Residual Solvents, 1998, No. 307, pp. 1-11.
Decision of Refusal for the corresponding JP patent application No. 2017-149671, dated May 2018.
(Continued)

*Primary Examiner* — Barbara P Badio
(74) *Attorney, Agent, or Firm* — Rothwell, Figg, Ernst & Manback, P.C.

(57) ABSTRACT

An object of the present invention is to provide a crystal of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one, which is useful as an antitumor agent, the crystal being stable, excellent in oral absorbability, highly chemically pure, and suitable for mass production. The present invention provides a crystal of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one that exhibits an X-ray powder diffraction spectrum containing at least three characteristic peaks at diffraction angles (2θ±0.2°) selected from 9.5°, 14.3°, 16.7°, 19.1°, 20.8°, 21.9°, and 25.2°. The present invention also provides a crystal of (S)-1-(3-(4-amino-3-((3, 5-dimethoxyphenyl)ethynyl)-1H-pyrazolo[3,4-d]pyrimidin-1-yl)-1-pyrrolidinyl)-2-propen-1-one that exhibits an X-ray powder diffraction spectrum containing at least seven characteristic peaks at diffraction angles (2θ±0.2°) selected from 13.5°, 17.9°, 19.5°, 20.6°, 22.0°, 22.6°, 23.3°, 23.7°, and 24.2°.

12 Claims, 6 Drawing Sheets

(56) References Cited

OTHER PUBLICATIONS

Xie et al., "FGFR2 Gene Amplification in Gastric Cancer Predicts Sensitivity to the Selective FGFR Inhibitor AZD4547", Clinical Cancer Research, vol. 19, No. 9, pp. 2572-2583 (2013).

Byron et al., "Fibroblast Growth Factor Receptor Inhibition Synergizes with Paclitaxel and Doxorubicin in Endometrial Cancer Cells", International Journal of Gynecological Cancer, vol. 22, No. 9, pp. 1517-1526 (2012).

Hernandez et al., "Prospective Study of FGFR3 Mutations as a Prognostic Factor in Nonmuscle invasive Urothelial Bladder Carcinomas", Journal of Clinical Oncology, 2006, vol. 24, No. 22, pp. 3664-367.

Gelsi-Boyer et al., "Comprehensive Profiling of 8p11-12 Amplification in Breast Cancer", Molecular Cancer Research, 2005, vol. 3, No. 12, pp. 655-667.

Turner et al., "FGFR1 Amplification Drives Endocrine Therapy Resistance and is a Therapeutic Target in Breast Cancer", Cancer Research, 2010, vol. 70, No. 5, pp. 2085-2094.

Wilson et al., "Widespread potential for growth-factor-driven resistance to anticancer kinase inhibitors", Nature, 2012, 487(7408): 505-509.

Chang et al., "Multiple receptor tyrosine kinase activation attenuates therapeutic efficacy of the fibroblast growth factor receptor 2 inhibitor AZD4547 in FGFR2 amplified gastric cancer", Oncotarget, vol. 6, No. 4, pp. 2009-2022.

Kleespies et al., "Tyrosine kinase inhibitors and gemcitabine: New treatment options in pancreatic cancer?", Drug Resistance Updates, 2006, pp. 1-18.

Office Action for the corresponding RU patent application No. 2016105133, dated Feb. 27, 2018, 9 pages.

Folkman, "Angiogenesis in cancer, vascular, rheumatoid and other diseases", Nature Medicine, 1995, vol. 1, No. 1, pp. 27-31 (cited in the International Search Report of PCT/JP2013/050740).

Lieu et al., "Beyond VEGF: Inhibition of the fibroblast growth factor pathway and antiangiogenesis", Clinical Cancer Research, 2011, vol. 17, No. 19, pp. 6130-6139 (cited in the International Search Report of PCT/JP2013/050740).

International Search Report from PCT/JP2013/050740, dated Aug. 30, 2013, 7 pages.

Gong et al., "A novel 3-arylethynyl-substituted pyrido[2,3-b]pyrazine derivatives and pharmacophore model as Wnt2/3-catenin pathway inhibitors in a non-small-cell lung cancer cell lines", Bioorganic &Medicinal Chemistry, vol. 19, 2011, pp. 5639-5647.

Sootome et al., "Identification and Biological Characterization of a Highly Potent, Irreversible Inhibitor of FGFR, TAS-2985", European Journal of Cancer, 48:116, 2012.

Nakatsuru et al., "Significant in Vivo Antitumor Activity by a Highly Potent, Irreversible FGFR Inhibitor, TAS-2985", European Journal of Cancer, 2012, vol. 48, Suppl. 6, pp. 117.

Gangjee et al., "Synthesis of 5,7-disubstituted-4-methyl-7H-pyrrolo[2,3-d]pyrimidin-2-amines as microtubule inhibitors", Bioorganic & Medicinal Chemistry, 2013, 3, vol. 21, No. 5, pp. 1180-1189.

Fukumoto et al., "FGF23 is a hormone-regulating phosphate metabolism—Unique biological characteristics of FGF23", Bone, 2007, vol. 40, pp. 1190-1195.

Shimada et al., "Targeted ablation of FGF23 demonstrates an essential physiological role of FGF23 in phosphate and vitamin D metabolism", Journal of Clinical Investigation, 2004, vol. 113, No. 4, pp. 561-568.

Razzaque et al., "FGF-23, vitamin D and calcification: the unholy triad", Nephrol. Dial. Transplant., 2005, vol. 20, pp. 2032-2035.

Jonker et al., "A phase I study to determine the safety, pharmacokinetics and pharmacodynamics of a dual VEGFR and FGFR inhibitor, brivanib, in patients with advanced or metastatic solid tumors", Annals of Oncology 22: pp. 1413-1419, 2011.

Pharmacodia TAS-120 (http://en.pharmacodia.com/web/drug/1_1258.html , retrived Jun. 10, 2017), 2 pages.

Cayman TAS 120 (https://www.caymanchem.com/product/21136, retrived Jun. 10, 2017)(cited in the specification of U.S. Appl. No. 14/905,420), 4 pages.

Konecny et al., "Activity of the Fibroblast Growth Factor Receptor Inhibitors Dovitinib (TK1258) andNVP-BGJ398 in Human Endometrial Cancer Cells", Molecular Cancer Therapeutics 12(5); 632-642, 2013(cited in the specification of U.S. Appl. No. 14/905,420).

Caira M R, "Crystalline Polymorphism of Organic Compounds", Topics in Current Chemistry, 1998, pp. 163-208.

Office Action dated Feb. 5, 2019 for the corresponding MX patent application No. MX/a/2017/012568, 9 pages.

Yuki Kagobutsu Kessho Sakusei Handbook—Genri to Know-how-, Maruzen Co., Ltd., 2008, pp. 57-84 (relevance is discussed in the Office Action dated Feb. 7, 2017, for the corresponding JP patent application No. 2016-566309).

Office Action dated Feb. 7, 2017, for the corresponding JP patent application No. 2016-566309.

Byrn et al., "Pharmaceutical Solids: A Strategic Approach to Regulartory Considerations", Pharmaceutical Research, 1995, 12(7), pp. 945-954.

Bavin, "Polymorphism in Process Development", Chemistry & Industry, 1989, (16), pp. 527-529.

Keiko Toyo Seizai no Sekkei to Hyoka, Kabushiki Kaisha Yakugyo Jihosha, 1995, pp. 76-79, 171-172 (relevance is discussed in the Office Action dated Feb. 7, 2017, for the corresponding JP patent application No. 2016-566309).

Byron et al., "The N550K/H Mutations in FGFR2 Confer Differential Resistance to PD173074, Dovitinib, and Ponatinib ATP-Competitive Inhibitors", Neoplasia, vol. 15, No. 8, Aug. 2013, pp. 975-988.

Office Action cited in U.S. Appl. No. 16/149,522, dated Jun. 26, 2019, 19 pages.

CRYSTAL OF 3,5-DISUBSTITUTED BENZENE ALKYNYL COMPOUND

CROSS REFERENCE TO RELATED APPLICATION

This application is a 35 U.S.C. 371 National Phase Entry Application from PCT/JP2016/060844, filed Mar. 31, 2016, which claims the benefit of Japanese Patent Application No. 2015-070927 filed on Mar. 31, 2015, the disclosures of which are incorporated herein in their entirety by reference.

TECHNICAL FIELD

The present invention relates to novel crystals of 3,5-disubstituted benzene alkynyl compound that are stable, excellent in oral absorbability, and useful as an antitumor agent.

BACKGROUND ART

Pharmaceutical compositions for oral administration are typically required to exhibit not only stability of the active ingredient, but also excellent absorbability during oral administration; and mass production methods of the compositions are also required.

In crystals, there may be polymorphs that contain the same molecule but have different molecular arrangements. Such polymorphs are known to exhibit different peaks in X-ray powder diffraction measurement (XRD measurement). Additionally, those crystal polymorphs are known to exhibit different solubility, oral absorbability, stability, and the like. Thus, optimal crystals must be found from different perspectives in developing drugs.

At present, a number of FGFR inhibitors are reported as antitumor agents, and Patent Literature 1, 2, and 3 disclose (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one (hereinafter "compound 1") as a compound that has excellent FGFR inhibitory activity and that exhibits antitumor activity.

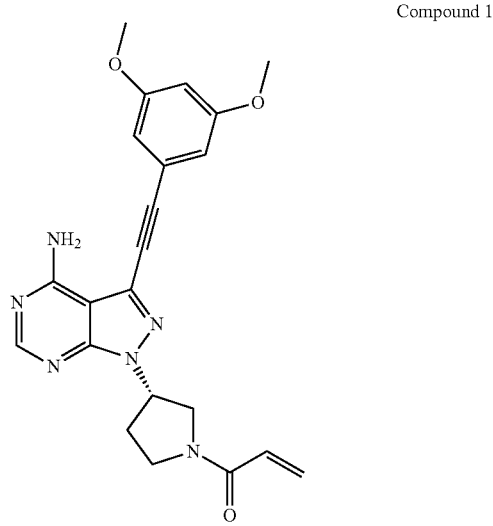 [SMILES: C=CC(=O)N1CC[C@H](n2nc(C#Cc3cc(OC)cc(OC)c3)c3c(N)ncnc32)C1]

Compound 1

However, none of Patent Literature 1, 2, or 3 discloses or suggests the crystal of compound 1, and the stability, oral absorbability, and crystallization method of the crystal.

CITATION LIST

Patent Literature

Patent Literature 1: WO2013/108809 pamphlet
Patent Literature 2: WO2015/008844 pamphlet
Patent Literature 3: WO2015/008839 pamphlet

SUMMARY OF INVENTION

Technical Problem

An object of the present invention is to provide a crystal of compound 1, which is useful as an antitumor agent and disclosed in Patent Literature 1, the crystal being stable, excellent in oral absorbability, and suitable for mass production; and to provide a method for crystallizing compound 1.

Solution to Problem

The present inventors conducted extensive research, and found that compound 1 has three crystalline forms (crystal I, crystal II, crystal III). The inventors found that among these, crystal II exhibits high stability, excellent oral absorbability, high crystallinity, high chemical purity, and is suitable for mass production, with homogenous particle size distribution; they thereby completed the invention. They also found that crystal II can be obtained by adding a specific solvent to compound 1 to crystallize it. They also found that crystal I of compound 1 exhibits high stability and excellent oral absorbability.

Specifically, the present invention provides the following Items.

Item 1.
A crystal of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one, the crystal exhibiting an X-ray powder diffraction spectrum containing at least three characteristic peaks at diffraction angles (2θ±0.2°) selected from 9.5°, 14.3°, 16.7°, 19.1°, 20.8°, 21.9°, and 25.2°.

Item 2.
The crystal according to Item 1, which exhibits an X-ray powder diffraction spectrum containing at least five characteristic peaks at diffraction angles (2θ±0.2°) selected from 9.5°, 14.3°, 16.7°, 19.1°, 20.8°, 21.9°, and 25.2°.

Item 3.
The crystal according to Item 1 or 2, which exhibits an X-ray powder diffraction spectrum containing characteristic peaks at diffraction angles (2θ±0.2°) of 9.5°, 14.3°, 16.7°, 19.1°, 20.8°, 21.9°, and 25.2°.

Item 4.
The crystal according to any one of Items 1 to 3, which has a chemical purity of 99.0% or more.

Item 5.
The crystal according to any one of Items 1 to 4, which exhibits an endothermic peak (the highest peak value) in the vicinity of 166° C. in differential scanning calorimetry measurement.

Item 6.
A pharmaceutical composition comprising the crystal according to any one of Items 1 to 5.

Item 7.
A pharmaceutical composition for oral administration, the composition comprising the crystal according to any one of Items 1 to 5.

Item 8.

A crystal of (S)-1-(3-(4-amino-3-((3,5-dimethoxyphenyl) ethynyl)-1H-pyrazolo[3,4-d]pyrimidin-1-yl)-1-pyrrolidinyl)-2-propen-1-one, the crystal exhibiting an X-ray powder diffraction spectrum containing at least seven characteristic peaks at diffraction angles (2θ±0.2°) selected from 13.5°, 17.9°, 19.5°, 20.6°, 22.0°, 22.6°, 23.3°, 23.7°, and 24.2°.

Item 9.

The crystal according to Item 8, which exhibits an X-ray powder diffraction spectrum containing characteristic peaks at diffraction angles (2θ±0.2°) of 13.5°, 17.9°, 19.5°, 20.6°, 22.0°, 22.6°, 23.3°, 23.7°, and 24.2°.

Item 10.

The crystal according to Item 8 or 9, which exhibits an endothermic peak (the highest peak value) in the vicinity of 169° C. in differential scanning calorimetry measurement.

Item 11.

A pharmaceutical composition comprising the crystal according to any one of Items 8 to 10.

Item 12.

A pharmaceutical composition for oral administration, the composition comprising the crystal according to any one of Items 8 to 10.

Item 13.

A crystal of (S)-1-(3-(4-amino-3-((3,5-dimethoxyphenyl) ethynyl)-1H-pyrazolo[3,4-d]pyrimidin-1-yl)-1-pyrrolidinyl)-2-propen-1-one, the crystal being produced by a method comprising step (1) of adding (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one to one or more solvents selected from the group consisting of water, $C_{1-4}$ alcohols, $C_{3-5}$ aliphatic carboxylic acid esters, $C_{3-6}$ ketones, $C_{2-5}$ aprotic polar organic solvents, and mixtures of these solvents, and step (2) of stirring the solvent to which (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one has been added in step (1) to crystallize (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one.

Item 14.

The crystal according to Item 13, which exhibits an X-ray powder diffraction spectrum containing at least three characteristic peaks at diffraction angles (2θ±0.2°) selected from 9.5°, 14.3°, 16.7°, 19.1°, 20.8°, 21.9°, and 25.2°.

Item 15.

The crystal according to Item 13 or 14, which has a chemical purity of 99.0% or more.

Item 16.

The crystal according to any one of Items 13 to 15, which exhibits an endothermic peak (the highest peak value) in the vicinity of 166° C. in differential scanning calorimetry measurement.

Item 17.

A method for crystallizing (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one, the method comprising step (1) of adding (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one to one or more solvents selected from the group consisting of water, $C_{1-4}$ alcohols, $C_{3-5}$ aliphatic carboxylic acid esters, $C_{3-6}$ ketones, $C_{2-5}$ aprotic polar organic solvents, and mixtures of these solvents, and step (2) of stirring the solvent to which (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one has been added in step (1) to crystallize (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one.

Item 18.

The crystallization method according to Item 17, wherein the crystal of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one obtained in step (2) exhibits an X-ray powder diffraction spectrum containing at least three characteristic peaks at diffraction angles (2θ±0.2°) selected from 9.5°, 14.3°, 16.7°, 19.1°, 20.8°, 21.9°, and 25.2°.

Item 19.

The crystallization method according to Item 17 or 18, wherein the crystal of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one obtained in step (2) has a chemical purity of 99.0% or more.

Item 20.

The crystallization method according to any one of Items 17 to 19, wherein the crystal of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one obtained in step (2) exhibits an endothermic peak (the highest peak value) in the vicinity of 166° C. in differential scanning calorimetry measurement.

Item 21.

A method for reducing scaling of a crystal of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one, the method comprising step (1) of adding (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one to a solvent selected from the group consisting of water, $C_{1-4}$ alcohols, $C_{3-5}$ aliphatic carboxylic acid esters, $C_{3-6}$ ketones, $C_{2-5}$ aprotic polar organic solvents, and mixtures of these solvents, and step (2) of stirring the solvent to which (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one has been added in step (1) to crystallize (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one.

Item 22.

The method for reducing scaling of a crystal according to Item 21, wherein the crystal of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one obtained in step (2) exhibits an X-ray powder diffraction spectrum containing at least three characteristic peaks at diffraction angles (2θ±0.2°) selected from 9.5°, 14.3°, 16.7°, 19.1°, 20.8°, 21.9°, and 25.2°.

Item 23.

The method for reducing scaling of a crystal according to Item 21 or 22, wherein the crystal of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one obtained in step (2) has a chemical purity of 99.0% or more.

Item 24.

The method for reducing scaling of a crystal according to any one of Items 21 to 23, wherein the crystal of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one obtained in step (2) exhibits an endothermic peak (the highest peak value) in the vicinity of 166° C. in differential scanning calorimetry measurement.

Item 25.

A crystal of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one, the crystal being obtainable by a method comprising step (1) of adding (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one to a solvent containing a $C_{7-10}$ hydrocarbon, a $C_{2-8}$ ether, a $C_{6-10}$ aliphatic carboxylic acid ester, or a mixture solvent of a $C_{7-10}$ hydrocarbon and a $C_{3-5}$ aliphatic carboxylic acid ester, and step (2) of stirring the solvent to which (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one has been added in step (1) to crystallize (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one.

Item 26.

The crystal according to Item 25, which exhibits an X-ray powder diffraction spectrum containing at least seven characteristic peaks at diffraction angles (2θ±0.2°) selected from 13.5°, 17.9°, 19.5°, 20.6°, 22.0°, 22.6°, 23.3°, 23.7°, and 24.2°.

Item 27.

The crystal according to Item 25 or 26, which exhibits an endothermic peak (the highest peak value) in the vicinity of 169° C. in differential scanning calorimetry measurement.

Item 28.

A method for crystallizing (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one, the method comprising step (1) of adding (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one to a solvent containing a $C_{5-10}$ hydrocarbon, a $C_{2-8}$ ether, a $C_{6-10}$ aliphatic carboxylic acid ester, or a mixture solvent of a $C_{5-10}$ hydrocarbon and a $C_{3-5}$ aliphatic carboxylic acid ester, and step (2) of stirring the solvent to which (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one has been added in step (1) to crystallize (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one.

Item 29.

The crystallization method according to Item 28, wherein the crystal of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one obtained in step (2) exhibits an X-ray powder diffraction spectrum containing at least seven characteristic peaks at diffraction angles (2θ±0.2°) selected from 13.5°, 17.9°, 19.5°, 20.6°, 22.0°, 22.6°, 23.3°, 23.7°, and 24.2°.

Item 30.

The crystal according to Item 28 or 29, wherein the crystal of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one obtained in step (2) exhibits an endothermic peak (the highest peak value) in the vicinity of 169° C. in differential scanning calorimetry measurement.

Advantageous Effects of Invention

Crystal II of compound 1 of the present invention exhibits high stability, excellent oral absorbability, high crystallinity, and high chemical purity, and is also suitable for mass production, with homogenous particle size distribution. Thus, crystal II can be used as an orally administered drug.

Additionally, crystal I of compound 1 exhibits high stability, excellent oral absorbability, high crystallinity, and high chemical purity. Thus, crystal I can be used as an orally administered drug.

DESCRIPTION OF EMBODIMENTS

Figure 1:
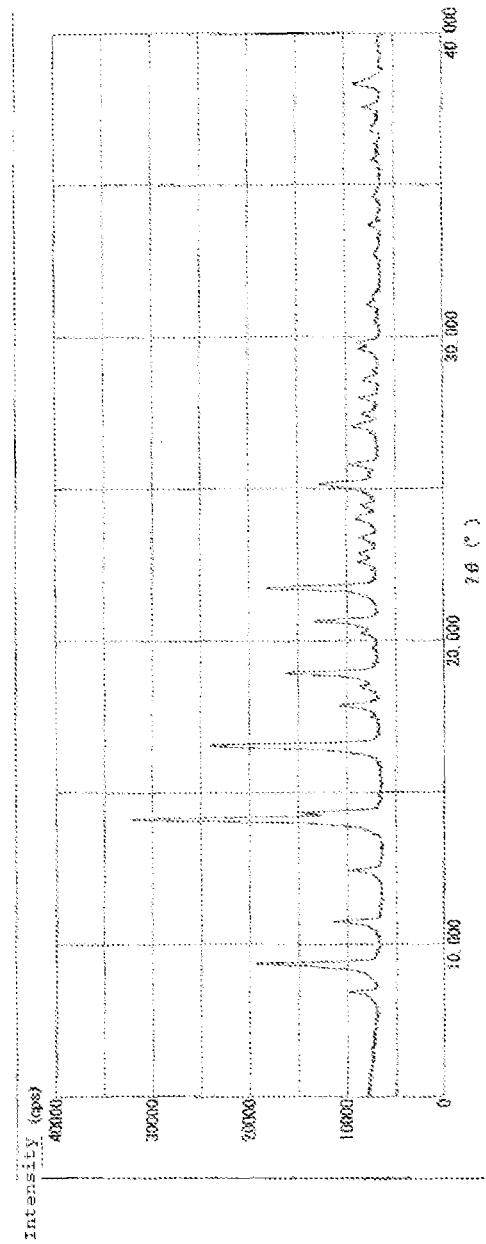
FIG. 1 illustrates an X-ray powder diffraction spectrum of crystal II of compound 1 (the vertical axis: intensity (cps), the horizontal axis: diffraction angle (2θ±0.2°)).

Compound 1 of the present invention can be synthesized by the production method disclosed in Patent Literature 1.

A crystal refers to a solid, in which atoms or molecules are arranged in an orderly repeating pattern, and differs from an amorphous solid, which does not have repeating units. Crystals and amorphous solids can be examined by methods such as X-ray powder diffraction measurement (XRD measurement), differential scanning calorimetry measurement (DSC measurement), thermogravimetric measurement-differential thermoanalysis (TG-DTA), or IR spectroscopy (IR).

In crystals, there may be polymorphs that contain the same molecule but have different molecular arrangements. Such polymorphs are known to exhibit peaks different from polymorphs in X-ray powder diffraction measurement (XRD measurement). Such polymorphs are also known to exhibit different solubility, oral absorbability, stability, and the like. Thus, optimal crystals must be found from different perspectives in developing drugs.

The present inventors conducted extensive research, and found that compound 1 has three crystal forms (crystal I, crystal II, and crystal III).

Crystal III can be obtained by using a mixture solvent of ethyl acetate and hexane. However, in the results of differential scanning calorimetry measurement (DSC measurement), crystal III exhibits an endothermic peak or exothermic peak in the vicinity of 145° C., which means that crystal III may be inferior to crystal I or crystal II in stability, and may undergo a change of crystal form, for example, during the production process or drug formation. Thus, crystal III is considered unsuitable as a crystal for drugs, which are required to be stable.

In contrast, DSC measurement of crystal I did not detect an endothermic peak or exothermic peak, and this confirmed that crystal I is a stable crystal, unlikely to undergo a change in crystal form, during drug formation and the like, and is chemically very stable. In addition, because of the extremely excellent oral absorbability, crystal I is suitable as a crystal for drugs, which are required to be stable and have excellent oral absorbability.

DSC measurement of crystal II also did not detect an endothermic peak or exothermic peak, and this confirmed that crystal II is a stable crystal, unlikely to undergo a change in crystal form, during drug formation and the like, and is chemically very stable. In addition, crystal II does not firmly adhere to equipment, such as a reactor and a stirring blade, during its precipitation in a solvent, and is suitable for mass production. Crystal II is also suitable for efficiently obtaining compound 1 with an extremely high chemical purity. Thus, crystal II is suitable as a crystal for drugs, for which a stable supply of a stable and highly pure crystal in high volumes is required.

Crystal I may be any crystal as long as crystal I contain crystal I of compound 1. Crystal II may be any crystal as long as crystal II contain crystal II of compound 1. Crystal I or crystal II may be a monocrystal of crystal I or crystal II, or a polymorphic mixture that contains other crystals. Specifically, 90 wt % or more of the crystal is preferably crystal I or crystal II, and more preferably, 95 wt % or more of the crystal is crystal I or crystal II, and particularly preferably, 99 wt % or more of the crystal is crystal I or crystal II.

In this specification, the term "chemical purity" refers to a purity measured by high-performance liquid chromatography, and a chemical purity of compound 1 indicates a purity determined by measuring compound 1 by high-performance liquid chromatography. The wavelength of the detector for use in purity measurement can be suitably determined. Specifically, the chemical purity of a crystal of compound 1 is preferably 95.0% or more, more preferably 98.0% or more, and particularly preferably 99.0% or more.

Crystal I and crystal II of the present invention each include those with different crystal habits (i.e., different external shapes) due to different growth of the crystal surface. Thus, crystal I and crystal II each include crystals that exhibit different relative intensities of peaks, even if the peak patterns at diffraction angle 2θ of crystal I or crystal II determined by XRD measurement are the same. The relative intensity used here refers to a value of each peak area relative to the largest peak area (taken as 100), among peaks at diffraction angle 2θ, in an X-ray powder diffraction spectrum.

The error of peaks at diffraction angle 2θ in X-ray powder diffraction spectrum in the present invention is about ±0.2°. This is an error caused by the devices used in measurement, sample adjustment, methods of data analysis, etc. Thus, the XRD measurement values of the crystals of the present invention include an error±0.2° in the values at diffraction angle 2θ.

The endothermic peak (the highest peak value) measured in DSC may vary depending on the temperature increase rate per minute, the weight of the sample, the purity of the sample, and other factors. In this specification, the term "in the vicinity of" means±5.0° C.

Crystal II of the present invention can be obtained by adding compound 1 to a specific solvent, and stirring the mixture to crystallize compound 1. Thus, the present invention provides a crystallization method to provide crystal II, the method comprising:
step (1) of adding compound 1 to a solvent; and
step (2) of stirring the solvent to which compound 1 has been added in step (1) to crystallize compound 1.

This method may also be paraphrased as a method for reducing scaling of a crystal of compound 1, the method comprising:
step (1) of adding compound 1 to a solvent; and
step (2) of stirring the solvent to which compound 1 has been added in step (1) to crystallize compound 1, thereby obtaining crystal II.

Solvents usable for crystallization to obtain crystal I of the present invention include $C_{7-10}$ hydrocarbons, $C_{2-8}$ ethers, $C_{6-10}$ aliphatic carboxylic acid esters, and mixture solvents of $C_{7-10}$ hydrocarbons and $C_{3-5}$ aliphatic carboxylic acid esters.

$C_{7-10}$ hydrocarbons refer to hydrocarbons having 7 to 10 carbon atoms, and examples include heptane and decane, with heptane being preferable.

$C_{2-8}$ ethers refer to ethers having 2 to 8 carbon atoms, and examples include diethyl ether, tert-butyl methyl ether, cyclopentyl methyl ether, and tetrahydrofuran, with tert-butyl methyl ether being preferable.

$C_{6-10}$ aliphatic carboxylic acid esters refer to aliphatic carboxylic acid esters having 6 to 10 carbon atoms in the entire esters, and examples include butyl acetate, pentyl acetate, hexyl acetate, octyl acetate, and butyl propionate, with butyl acetate being preferable.

$C_{3-5}$ aliphatic carboxylic acid esters refer to aliphatic carboxylic acid esters having 3 to 5 carbon atoms in the entire esters, and examples include methyl acetate, ethyl acetate, propyl acetate, isopropyl acetate, methyl propionate, and ethyl propionate, with ethyl acetate being preferable.

Solvents usable for crystallization to obtain crystal I of the present invention include solvents selected from the group consisting of $C_{7-10}$ hydrocarbons, $C_{2-8}$ ethers, $C_{6-10}$ aliphatic carboxylic acid esters, $C_{7-10}$ hydrocarbons-$C_{3-5}$ aliphatic carboxylic acid esters, and mixtures of these solvents, with heptane, tert-butyl methyl ether, butyl acetate, and a mixture solvent of heptane-ethyl acetate being preferable.

Solvents usable for obtaining crystal II of the present invention include solvents selected from the group consisting of water, $C_{1-4}$ alcohols, $C_{3-5}$ aliphatic carboxylic acid esters, $C_{3-6}$ ketones, $C_{2-5}$ aprotic polar organic solvents, and mixtures of these solvents.

$C_{1-4}$ alcohols refer to alcohols having 1 to 4 carbon atoms, and examples include methanol, ethanol, n-propanol, isopropanol, n-butanol, and t-butanol, with ethanol and isopropanol being preferable.

$C_{3-5}$ aliphatic carboxylic acid esters refer to the aforementioned aliphatic carboxylic acid esters, and ethyl acetate is preferable.

$C_{3-6}$ ketones refer to ketones having 3 to 6 carbon atoms in the entire ketones, and examples include acetone, methyl ethyl ketone, methyl isobutyl ketone, and cyclohexanone, with acetone and methyl ethyl ketone being preferable.

$C_{2-5}$ aprotic polar organic solvents include acetonitrile, N-methyl-2-pyrrolidone, N,N-dimethylformamide, N,N-dimethylacetamide, and dimethyl sulfoxide.

Solvents usable for crystallization to obtain crystal II of the present invention include solvents selected from the group consisting of water, $C_{1-4}$ alcohols, $C_{3-5}$ aliphatic carboxylic acid esters, $C_{3-6}$ ketones, $C_{2-5}$ aprotic polar organic solvents, and mixtures of these solvents, with solvents selected from the group consisting of water, $C_{1-4}$ alcohols, $C_{3-5}$ aliphatic carboxylic acid esters, $C_{3-6}$ ketones, and mixtures of these solvents being preferable. More preferable solvents include ethanol, isopropanol, acetone, methyl ethyl ketone, ethyl acetate, and a mixture solvent of water-ethanol. A particularly preferable solvent is a mixture solvent of water-ethanol. In the use of a mixture solvent of water-$C_{1-4}$ alcohol, the ratio of $C_{1-4}$ alcohol to water can suitably be adjusted such that a $C_{1-4}$ alcohol is present in an amount of typically 0.01 to 100 parts by weight, preferably 0.1 to 50 parts by weight, and more preferably 1 to 30 parts by weight, per part by weight of water.

The amount of a solvent to be added to crystal I or crystal II of the present invention is, from the standpoint of crystal yield, 1 to 100 times (volume/weight), preferably 2 to 50 times (volume/weight), and more preferably 4 to 30 times (volume/weight) as much as the mass of compound 1.

The temperature for crystallization to obtain crystal I or crystal II of the present invention can suitably be determined according to the solvent for use within the range of 0° C. to the boiling point of the solvent. The temperature for crystallization does not necessarily stay same temperature, and heating or cooling can be performed between 0° C. to the boiling point of the solvent. Heating used here means maintaining the temperature of the solvent at 40° C. or more, and cooling means maintaining the temperature of the solvent at less than 15° C.

Stirring for crystallization to obtain crystal I or crystal II of the present invention can suitably be performed using a stirrer, a stirring blade, a magnetic stirrer, or other stirrers, according to the amount of the solvent, and the size of the reaction furnace, and the like. The stirring rate is typically 1 to 600 rpm, and preferably 10 to 300 rpm.

The stirring time for crystallization to obtain crystal I or crystal II of the present invention is preferably a predetermined length of time or more to sufficiently facilitate the crystallization and to obtain the crystal at high yield, and preferably less than a predetermined length of time to reduce the decomposition of the crystal, which decreases the yield. The stirring time is, 1 minute to 120 hours, preferably 1 to 72 hours, and more preferably 3 to 48 hours.

Reducing scaling of crystal II in crystallization according to the present invention means reducing the amount of the crystal remaining in the reactor to less than 20% of the theoretical yield; the amount is preferably less than 10%, and more preferably less than 5% of the theoretical yield.

Crystal I or crystal II of the present invention precipitated in a solvent can be isolated and purified by known separation and purification techniques, such as filtration, washing with an organic solvent, and drying under reduced pressure. The organic solvents for use in washing include the solvents described above, and the organic solvents are preferably ethanol, isopropanol, acetone, methyl ethyl ketone, ethyl acetate, and a mixture solvent of water-ethanol. The atmospheric pressure for drying under reduced pressure is 0.1 atm or less, and preferably 0.05 atm or less. The temperature for drying under reduced pressure is 0 to 200° C., and preferably 25 to 100° C.

For crystallization of the present invention, crystal I or crystal II may be added as a seed crystal. The seed crystal to be added is 0.1 to 10 wt %, and preferably 1 to 3 wt % of the theoretical yield of crystallized compound 1.

Figure 2:
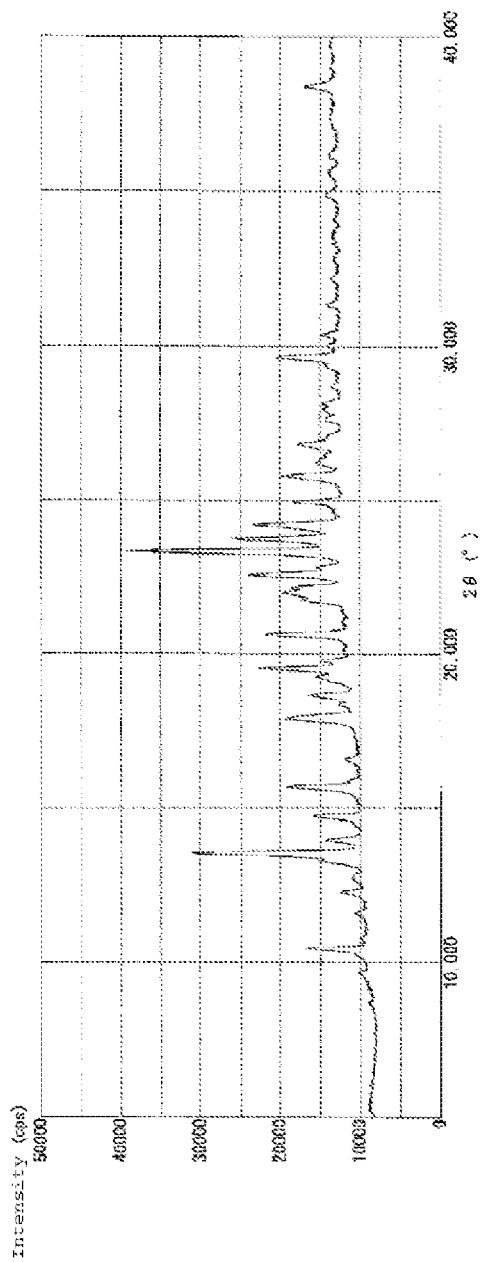
FIG. 2 illustrates an X-ray powder diffraction spectrum of crystal I of compound 1 (the vertical axis: intensity (cps), the horizontal axis: diffraction angle (2θ±0.2°)).

The thus-obtained crystal I of compound 1 exhibits an X-ray powder diffraction spectrum containing at least seven peaks at diffraction angles (2θ±0.2°) selected from 13.5°, 17.9°, 19.5°, 20.6°, 22.0°, 22.6°, 23.3°, 23.7°, and 24.2°. More preferably, as shown in FIG. 2, crystal I of compound 1 exhibits an X-ray powder diffraction spectrum containing characteristic peaks at diffraction angles (2θ±0.2°) of 13.5°, 17.9°, 19.5°, 20.6°, 22.0°, 22.6°, 23.3°, 23.7°, and 24.2°. In a typical embodiment, crystal I of compound 1 exhibits an endothermic peak (the highest peak value), for example, in the vicinity of 164 to 174° C., more preferably in the vicinity of 169° C., as shown in the result of differential scanning calorimetry measurement (DSC measurement) in FIG. 5.

The thus-obtained crystal I of compound 1 exhibits an X-ray powder diffraction spectrum containing at least seven peaks at diffraction angles (2θ±0.2°) selected from 13.5°, 17.9°, 19.5°, 20.6°, 22.0°, 22.6°, 23.3°, 23.7°, and 24.2°, and exhibits an endothermic peak (the highest peak value) in the vicinity of 164 to 174° C. in differential scanning calorimetry measurement (DSC measurement). More preferably, crystal I of compound 1 exhibits an X-ray powder diffraction spectrum containing characteristic peaks at diffraction angles (2θ±0.2°) of 13.5°, 17.9°, 19.5°, 20.6°, 22.0°, 22.6°, 23.3°, 23.7°, and 24.2° as shown in FIG. 2, and exhibits an endothermic peak (the highest peak value) in the vicinity of 169° C. in differential scanning calorimetry measurement (DSC measurement).

The thus-obtained crystal II of compound 1 exhibits an X-ray powder diffraction spectrum containing at least three peaks at diffraction angles (2θ±0.2°) selected from 9.5°, 14.3°, 16.7°, 19.1°, 20.8°, 21.9°, and 25.2°. More preferably, crystal II of compound 1 exhibits an X-ray powder diffraction spectrum containing at least five peaks at diffraction angles (2θ±0.2°) selected from 9.5°, 14.3°, 16.7°, 19.1°, 20.8°, 21.9°, and 25.2°. Still more preferably, crystal II of compound 1 exhibits an X-ray powder diffraction spectrum containing characteristic peaks at diffraction angles (2θ±0.2°) of 9.5°, 14.3°, 16.7°, 19.1°, 20.8°, 21.9°, and 25.2° as shown in FIG. 1. In a typical embodiment, crystal II of compound 1 exhibits an endothermic peak (the highest peak value), for example, in the vicinity of 161 to 171° C., and more preferably in the vicinity of 166° C. as shown in the result of differential scanning calorimetry measurement (DSC measurement) in FIG. 4.

Crystal II of the present invention exhibits an X-ray powder diffraction spectrum containing at least three peaks at diffraction angles (2θ±0.2°) selected from 9.5°, 14.3°, 16.7°, 19.1°, 20.8°, 21.9°, and 25.2°, and exhibits an endothermic peak (the highest peak value) in the vicinity of 161 to 171° C. in differential scanning calorimetry measurement (DSC measurement). More preferably, crystal II exhibits an X-ray powder diffraction spectrum containing at least five peaks at diffraction angles (2θ±0.2°) selected from 9.5°, 14.3°, 16.7°, 19.1°, 20.8°, 21.9°, and 25.2°, and exhibits an endothermic peak (the highest peak value) in the vicinity of 166° C. in differential scanning calorimetry measurement (DSC measurement). Still more preferably, crystal II exhibits an X-ray powder diffraction spectrum containing seven peaks at diffraction angles (2θ±0.2°) selected from 9.5°, 14.3°, 16.7°, 19.1°, 20.8°, 21.9°, and 25.2°, and exhibits an endothermic peak (the highest peak value) in the vicinity of 166° C. in differential scanning calorimetry measurement (DSC measurement).

Because of the excellent FGFR inhibitory activity of compound 1, crystal I and crystal II of the present invention are both useful as an antitumor agent. Although not particularly limited to, examples of the target cancer include head and neck cancer, gastroenterological cancer (e.g., esophageal cancer, stomach cancer, gastrointestinal stromal tumor, duodenal cancer, liver cancer, biliary tract cancer (e.g., gallbladder cancer, and bile duct cancer), pancreas cancer, small intestinal cancer, large intestinal cancer (e.g., colorectum cancer, colon cancer, and rectal cancer)), lung cancer, breast cancer, ovarian cancer, uterus cancer (e.g., cervical cancer and endometrial cancer), kidney cancer, bladder cancer, prostate cancer, urothelial cancer, bone and soft tissue sarcomas, blood cancer (e.g., B-cell lymphoma, chronic lymphocytic leukemia, peripheral T-cell lymphoma, myelodysplastic syndrome, acute myeloid leukemia, and acute lymphocytic leukemia), multiple myeloma, skin cancer, and mesothelioma.

To use crystal I or crystal II of the present invention as a drug, a pharmaceutical carrier may optionally be added to crystal I or crystal II to prepare a suitable dosage form according to the prevention or treatment purpose. Examples of the dosage form include oral drugs, injectable agents, suppositories, ointments, and patches, with oral drugs being preferable. These dosage forms can be prepared by methods known to a person skilled in the art.

The pharmaceutical carrier for use includes a range of organic or inorganic carrier substances commonly used for drug materials; and the carrier is added as an excipient, binder, disintegrant, lubricant, or colorant to solid drugs, or as a solvent, solubilizing agent, suspending agent, isotonic agent, buffer, or soothing agent to liquid drugs. Pharmaceutical preparation additives, such as preservatives, antioxidants, colorants, sweeteners, and stabilizers, may also optionally be added.

Oral solid drugs can be prepared by adding an excipient, optionally together with an excipient, binder, disintegrant, lubricant, colorant, taste-masking or flavoring agent, etc., to crystal I or crystal II of the present invention to produce tablets, coated tablets, granules, powders, capsules, or the like in accordance with an ordinary method.

Injectable agents can be prepared by adding a pH adjuster, buffer, stabilizer, isotonic agent, local anesthetic, etc., to crystal I or crystal II of the present invention, and processing the mixture to a subcutaneous, intramuscular, or intravenous injectable agent in accordance with an ordinary method.

The amount of crystal I or crystal II of the present invention to be added to each unit of dosage form varies depending on the symptoms of the patient who is administered the drug, or the dosage form. However, the desirable amount per unit of dosage form is typically 0.05 to 1000 mg for oral drugs, 0.01 to 500 mg for injectable agents, and 1 to 1000 mg for suppositories.

The daily dosage of a drug in dosage forms described above varies depending on the symptoms, body weight, age, gender of the patient, and so on; and cannot be generalized. However, the dosage based on the content of crystal I or crystal II of the present invention is typically 0.05 to 5000 mg, and preferably 0.1 to 1000 mg, per adult (body weight: 50 kg) per day, and it is preferable to administer the drug in one dose or in about two to three divided doses per day.

EXAMPLES

The following describes the present invention in more detail with reference to Examples; however, the present invention is not limited to these Examples. Although the present invention is sufficiently described in the Examples, a person skilled in the art would still be able to add various changes and/or modification thereto. Unless such changes and/or modification go beyond the scope of the present invention, the present invention encompasses such changes and/or modification.

The reagents used in the Examples are commercially available products, otherwise particularly indicated.

X-Ray Powder Diffraction Measurement (XRD Measurement)

X-ray powder diffraction of a test substance was measured under the following test conditions after lightly pulverizing some amount of the test substance in an agate mortar as necessary.
Device: Rigaku Corporation: RINT-ULTIMA+2100
Target: Cu
X-ray output: 40 mA, 40 kV
Scanning Range: 5.0 to 40.0°
Step Size: 0.010°
Scanning Speed: 5.00° C./min.
Divergence Slit: ½°
Scattering Slit: 3.00 mm
Receiving Slit: 13.00 mm The device and data were handled in accordance with the methods and procedures as instructed for the device.
Differential Scanning calorimetry Measurement (DSC Measurement)
DSC measurement was performed under the following conditions.
Device: TA Instruments Q1000
Sample: about 1 mg
Sample Container: made of aluminum
Temperature Increase Rate: 10° C./min
Atmospheric Gas: Nitrogen
Nitrogen Gas Flow: 50 ml/min The device and data were handled in accordance with the methods and procedures as instructed for the device.
High-Performance Liquid Chromatography
Measurement by high-performance liquid chromatography was performed under the following conditions.
Device: 1200 series binary LC system (Agilent Technologies)
Sample: 0.1 mg/mL 0.1% phosphoric acid aqueous solution—acetonitrile solution (1/1)
Mobile Phase A: 0.1% phosphoric acid aqueous solution
Mobile Phase B: acetonitrile
Column: Ascentis Express C18, 4.6×150 mm, S=2.7 μm
Measurement Wavelength: 210 nm The device and data were handled in accordance with the methods and procedures as instructed for the device.

The measurement by high-performance liquid chromatography was also performed under the following test conditions.
Device: ACQUITY SQD, Quadrupole (Waters)
Sample: 0.1 mg/mL acetonitrile solution
Mobile Phase A: 0.1% formic acid aqueous solution
Mobile Phase B: 0.1% formic acid-acetonitrile
Column: YMC-Triart C18, 2.0×50 mm, 1.9 μm (YMC)
Measurement Wavelength: 254 nm The device and data were handled in accordance with the methods and procedures as instructed for the device.

Example 1: Production of Crystal II of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one Ethanol (9 mL) and water (1 mL) were added to compound 1 (1.00 g) obtained by the method disclosed in Patent Literature 1, and the mixture was stirred at 75° C. for 5 minutes. Subsequently, the temperature was lowered to room temperature, and the mixture was stirred for 26 hours, followed by filtering the precipitate, thereby obtaining crystal II of compound 1 (771 mg, yield 77%).

Figure 4:
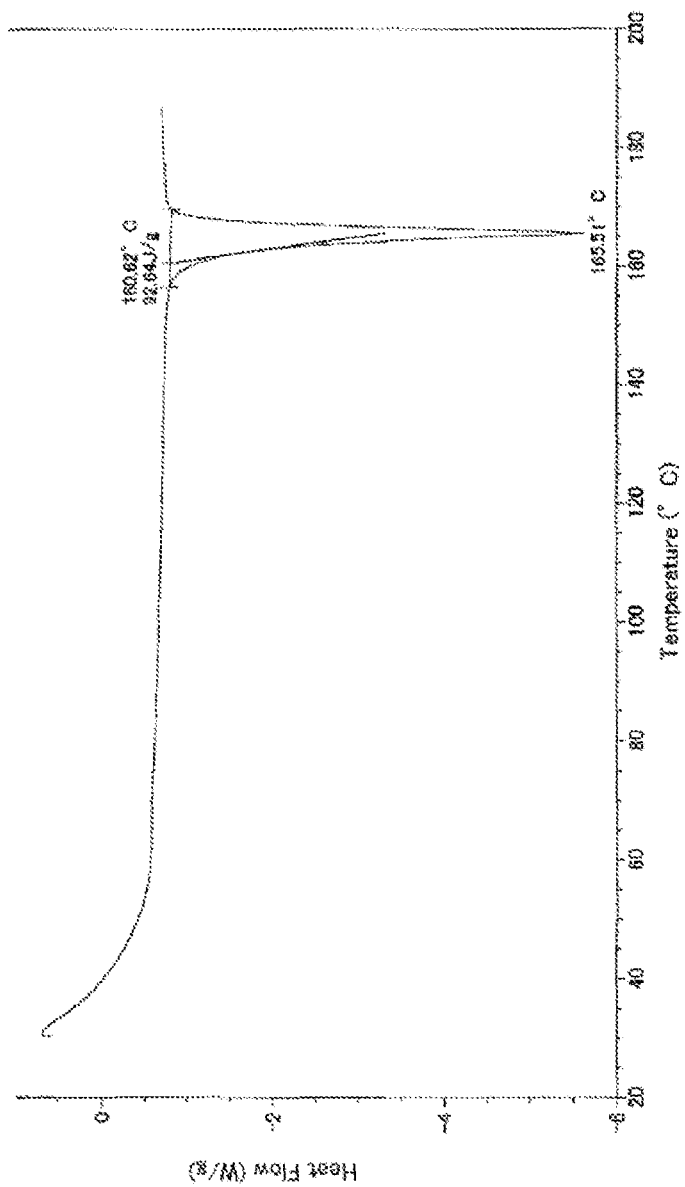
FIG. 4 illustrates a differential scanning calorimetry (DSC) curve of crystal II of compound 1.

As shown in FIG. 1, crystal II exhibited an X-ray powder diffraction spectrum containing characteristic peaks at diffraction angles (2θ±0.2°) of 9.5°, 14.3°, 16.7°, 19.1°, 20.8°, 21.9°, and 25.2°. As shown in FIG. 4, crystal II exhibited an endothermic peak (the highest peak value) in the vicinity of 166° C. in differential scanning calorimetry measurement (DSC measurement).

Example 2: Production of Crystal I of Compound 1 t-Butyl methyl ether (1 mL) was added to compound 1 (50 mg) obtained by the method disclosed in Patent Literature 1, and the mixture was stirred at room temperature for 20 hours, thereby obtaining crystal I of compound 1 (28 mg, yield 56%).

Figure 5:
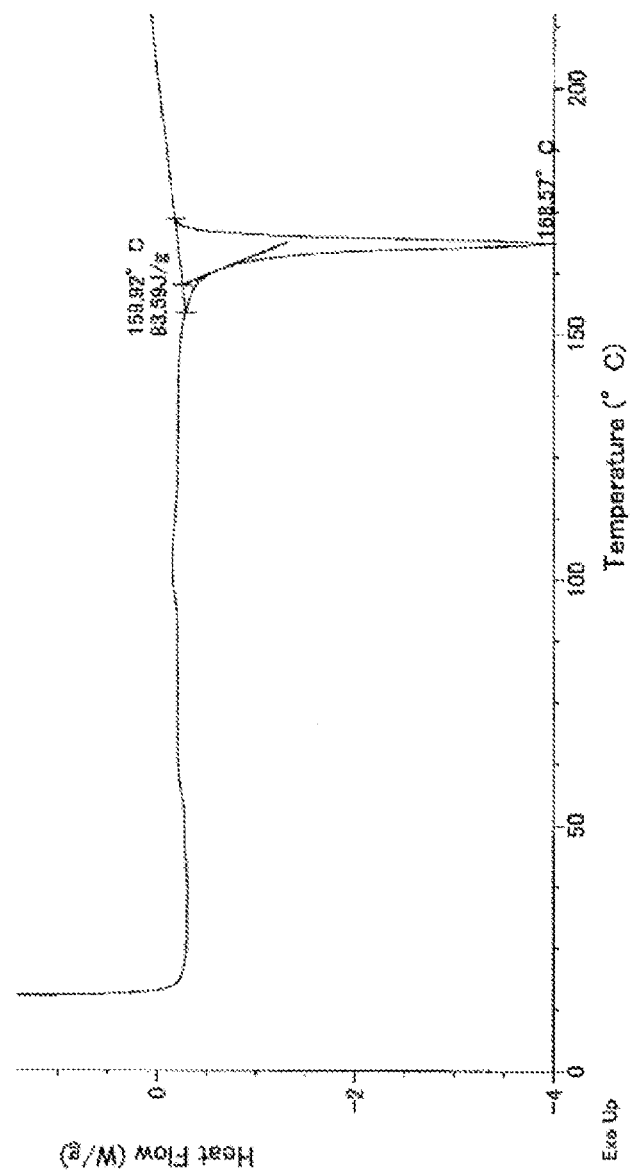
FIG. 5 illustrates a differential scanning calorimetry (DSC) curve of crystal I of compound 1.

As shown in FIG. 2, crystal I exhibited an X-ray powder diffraction spectrum containing characteristic peaks at diffraction angles (2θ±0.2°) of 13.5°, 17.9°, 19.5°, 20.6°, 22.0°, 22.6°, 23.3°, 23.7°, and 24.2°. As shown in FIG. 5, crystal I exhibited an endothermic peak (the highest peak value) in the vicinity of 170° C. in differential scanning calorimetry measurement (DSC measurement).

Comparative Example 1: Crystal III of Compound 1

From compound 1 (1.91 g) obtained by the method disclosed in Patent Literature 1, crystal III of compound 1 was prepared (821 mg, yield 43%) using a mixture solvent of ethyl acetate and n-hexane in the same manner as in Example 1.

Figure 3:
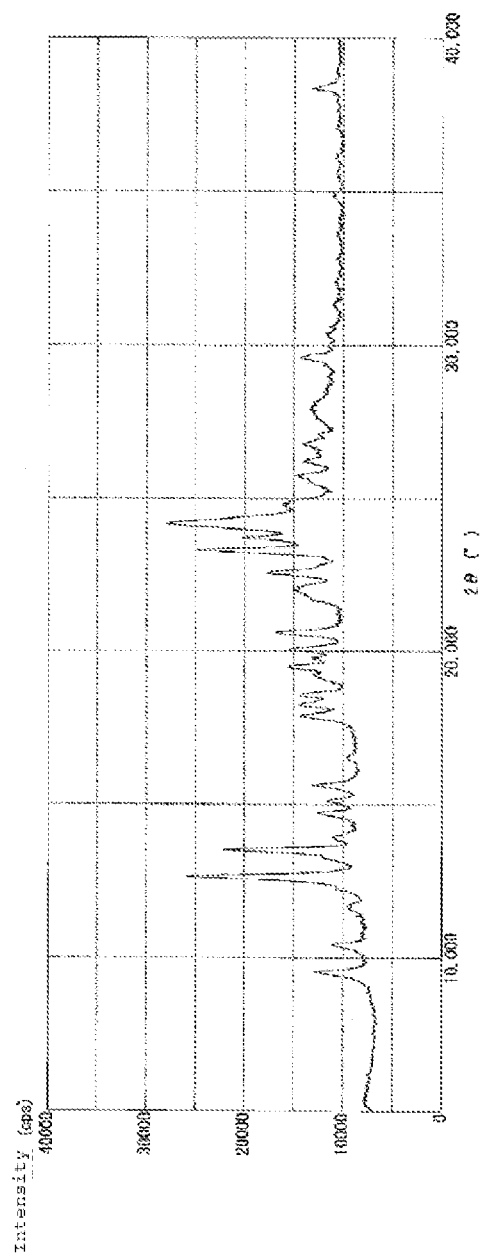
FIG. 3 illustrates an X-ray powder diffraction spectrum of crystal III of compound 1 (the vertical axis: intensity (cps), the horizontal axis: diffraction angle (2θ±0.2°)).
Figure 6:
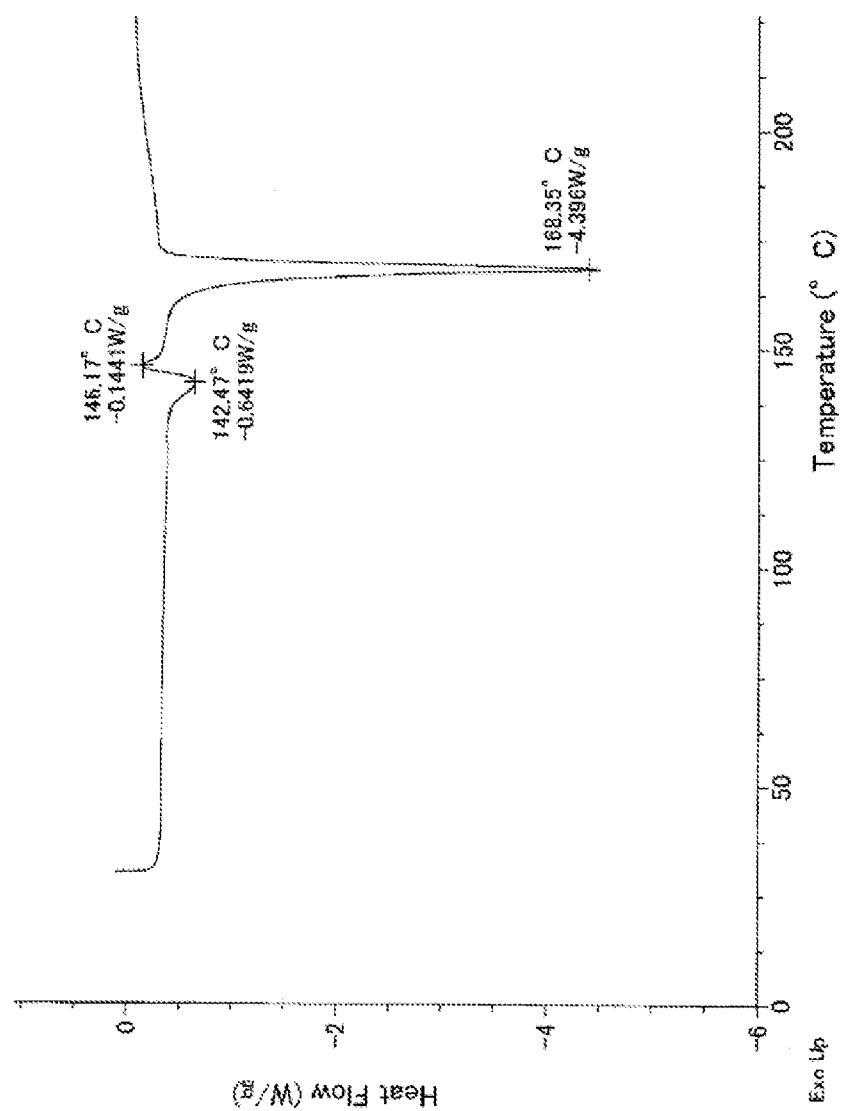
FIG. 6 illustrates a differential scanning calorimetry (DSC) curve of crystal III of compound 1.

As shown in FIG. 3, crystal III of compound 1 exhibited an X-ray powder diffraction spectrum containing characteristic peaks at diffraction angles (2θ±0.2°) of 9.5°, 12.6°, 13.5°, 20.1°, 20.6°, 22.5°, 23.3°, 23.7°, and 24.2°. As shown in FIG. 6, crystal III of compound 1 exhibited an endothermic peak (the highest peak value) in the vicinity of 140° C. and 170° C. in differential scanning calorimetry measurement (DSC measurement).

Test Example 1: Solid Stability of Crystal II of Compound 1

Crystal I and crystal II of compound 1 were left at 40° C., 40° C. (humidity 75%), or 60° C. for 1 month. Thereafter, their chemical purity was measured by high-performance liquid chromatography, and the change in chemical purity was 0.1% or less under every condition. In differential scanning calorimetry measurement (DSC measurement) of Examples 1 and 2 and Comparative Example 1, unlike crystal III of compound 1 shown in Comparative Example 1, crystal I and crystal II of compound 1 did not exhibit a peak that suggests a phase transition when the temperature was increased. These results indicate that crystal I and crystal II of compound 1 have excellent solid stability.

Test Example 2: Oral Absorbability of Crystal II of Compound 1

Crystal I and crystal II of compound 1 were individually suspended in a 0.5% HPMC aqueous solution, and orally administered to BALB/c mice in a dosage of 50 mg/kg. After 0.5, 1, 2, 4, and 6 hours from administration, blood of each mouse was collected from the retro-orbital sinus, and the concentration of compound 1 in plasma was measured. Table 1 shows the results. The oral absorbability of both crystal I and crystal II of compound 1 was excellent, with oral absorbability of crystal I being better. The oral absorbability of both crystal I and crystal II was also confirmed to have achieved a sufficient concentration that provides a medicinal effect.

TABLE 1

|  | Crystal I | Crystal II |
| --- | --- | --- |
| AUC μM · hr | 9.82 | 4.99 |

Test Example 3: Chemical Purity Comparison Between Crystal I and Crystal II of Compound 1 from the Same Lot Crude compound 1 (50 mg, chemical purity 98.6%) obtained by the method disclosed in Patent Literature 1 was added to 1 mL of acetone, and the mixture was stirred at room temperature for 20 hours, followed by filtering the precipitate, thereby obtaining crystal II of compound 1.

Likewise, crude compound 1 obtained as described above was added to ethyl acetate, and the mixture was stirred at room temperature for 20 hours, followed by filtering the precipitate, thereby obtaining crystal II of compound 1.

Crude compound 1 obtained as described above was added to tert-butyl methyl ether, and the mixture was stirred at room temperature for 20 hours, followed by filtering the precipitate, thereby obtaining crystal I of compound 1.

Table 2 shows the chemical purity of crude compound 1, and crystal II and crystal I of compound 1 obtained from crude compound 1 using the respective solvents. Recrystallization is typically expected to increase the chemical purity, and these results indicate that crystal II is a crystal from which impurities can efficiently be removed. Because guideline ICH-Q3A of the International Council for Harmonisation of Technical Requirements for Pharmaceuticals for Human Use (Japan, US, and Europe) specifies 0.03% or more of impurities in a drug substance as being subject to regulation, the results of the test examples are useful.

TABLE 2

|  | Crude Compound 1 | Crystal II | | Crystal I |
|  |  | Acetone | Ethyl Acetate | TBME |
| --- | --- | --- | --- | --- |
| Chemical Purity (%) | 98.7 | 99.0 | 99.1 | 98.4 |

Test Example 4: Scaling Comparison Between Crystal I and Crystal II of Compound 1

Crude compound 1 obtained by the method disclosed in Patent Literature 1 (prepared to give 767 mg as a theoretical yield) and a mixture solvent of ethyl acetate (30 mL) and heptane (24 mL) were added to a reactor, and heated to reflux for 1.5 hours. After cooling, only the precipitate dispersed in the solvent in the reactor was filtered to obtain crystal I of compound 1 (290 mg, yield 38%). Separately, the precipitate adhered to the reactor and other equipment (scaling) was collected and obtained crystal I of compound 1 (312 mg, yield 41%).

From crude compound 1, crystal II was prepared using a mixture solvent of water and ethanol, acetone, or ethyl acetate in the same manner, but the scaling of crystal II was less than 5%.

The results revealed that scaling that occurred during the production of crystal I of compound 1 accounted for about 40% of the yield, suggesting that scaling may cause decreases in the yield or malfunction of production equipment on an industrial scale. There was, however, no such suggestion of scaling problem for crystal II, and crystal II is considered suitable for mass production.

The invention claimed is:

1. A crystal of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one, the crystal exhibiting an X-ray powder diffraction spectrum containing at least three characteristic peaks at diffraction angles (2θ±0.2°) selected from 9.5°, 14.3°, 16.7°, 19.1°, 20.8°, 21.9°, and 25.2°.

2. The crystal according to claim 1, which exhibits an X-ray powder diffraction spectrum containing at least five characteristic peaks at diffraction angles (2θ±0.2°) selected from 9.5°, 14.3°, 16.7°, 19.1°, 20.8°, 21.9°, and 25.2°.

3. The crystal according to claim 1, which exhibits an X-ray powder diffraction spectrum containing characteristic peaks at diffraction angles (2θ±0.2°) of 9.5°, 14.3°, 16.7°, 19.1°, 20.8°, 21.9°, and 25.2°.

4. The crystal according to claim 1, which exhibits an endothermic peak (the highest peak value) in the vicinity of 166° C. in differential scanning calorimetry measurement.

5. A pharmaceutical composition comprising the crystal according to claim 1.

6. A pharmaceutical composition for oral administration, the composition comprising the crystal according to claim 1.

7. A crystal of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one, the crystal exhibiting an X-ray powder diffraction spectrum containing at least seven characteristic peaks at diffraction angles (2θ±0.2°) selected from 13.5°, 17.9°, 19.5°, 20.6°, 22.0°, 22.6°, 23.3°, 23.7°, and 24.2°.

8. The crystal according to claim 7, which exhibits an X-ray powder diffraction spectrum containing characteristic peaks at diffraction angles (2θ±0.2°) of 13.5°, 17.9°, 19.5°, 20.6°, 22.0°, 22.6°, 23.3°, 23.7°, and 24.2°.

9. The crystal according to claim 7, which exhibits an endothermic peak (the highest peak value) in the vicinity of 169° C. in differential scanning calorimetry measurement.

10. A pharmaceutical composition comprising the crystal according to claim 7.

11. A pharmaceutical composition for oral administration, the composition comprising the crystal according to claim 7.

12. A method for reducing scaling of a crystal of (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one, the method comprising
step (1) of adding (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one to a solvent selected from the group consisting of water, $C_{1-4}$ alcohols, $C_{3-5}$ aliphatic carboxylic acid esters, $C_{3-6}$ ketones, $C_{2-5}$ aprotic polar organic solvents, and mixtures of these solvents, and
step (2) of stirring the solvent to which (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one has been added in step (1) to crystallize (S)-1-(3-(4-amino-3-((3,5-dimethoxyphenyl)ethynyl)-1H-pyrazolo[3,4-d]pyrimidin-1-yl)-1-pyrrolidinyl)-2-propen-1-one.

* * * * *